United States Patent [19]
Bennetau et al.

[11] Patent Number: 5,334,753
[45] Date of Patent: Aug. 2, 1994

[54] PROCESSES FOR PREPARING ORTHO-SUBSTITUTED BENZOIC ACIDS

[75] Inventors: Bernard Bennetau, Talence Cedex, France; Paul A. Cain, Ongar, England

[73] Assignee: Rhone-Poulenc Agriculture Ltd, Essex, England

[21] Appl. No.: 996,046

[22] Filed: Dec. 23, 1992

Related U.S. Application Data

[63] Continuation-in-part of Ser. No. 850,128, Mar. 12, 1992, abandoned.

[51] Int. Cl.$^5$ .................. C07C 63/06; C07C 59/48
[52] U.S. Cl. .................. 562/405; 562/431; 562/471
[58] Field of Search ............ 562/431, 471, 405

[56] References Cited

U.S. PATENT DOCUMENTS 4,323,692  4/1982  Tanger .................. 558/257

FOREIGN PATENT DOCUMENTS 0418175  3/1991  European Pat. Off. .

OTHER PUBLICATIONS

Snieckus, *Chem. Rev.* 90, 879–933 (1990).
Gschwend et al, in *Organic Reactions*, eds. W. G. Dauben et al, John Wiley & Sons, Inc., New York, vol. 26, Chapter 1, p. 69 (1979).
Yu et al, *J. Chem. Soc. Perkin Trans.* I, 2600–2601 (1991).
Carpenter et al, *Tetrahedron Letters*, vol. 26, No. 14, 1777–1780 (1985).
Meyers et al, *Tetrahedron Letters*, vol. 24, No. 45, 4935–4938 (1983).
CA 94 (19):156485p o–Benzoylbenzoic acids . . . podophyllotoxin. Parham et al., p. 618, 1981.
Parham et al., *J. Org. Chem..*, 46, 1057–1061, 1981, o–Benzoylbenzoic Acids . . . Podophyllotoxin.

*Primary Examiner*—Mary C. Lee
*Assistant Examiner*—Joseph K. McKane
*Attorney, Agent, or Firm*—Burns, Doane, Swecker & Mathis

[57] ABSTRACT

A novel process for the synthesis of ortho-substituted benzoic acid by lithiating an unprotected benzoic acid and a number of novel orth-substituted benzoic acids are described.

12 Claims, No Drawings

PROCESSES FOR PREPARING ORTHO-SUBSTITUTED BENZOIC ACIDS

This application is a Continuation-in-Part of co-pending U.S. patent application Ser. No. 07/850,128 filed on Mar. 12, 1992 incorporated by reference herein, and now abandoned.

BACKGROUND OF THE INVENTION

1. Field of the Invention

This invention relates to a process for preparing certain ortho-substituted benzoic acids and to novel benzoic acids produced from this process.

2. Discussion of Background

The subject compounds are intermediates in the production of pesticides, for example as described in European Patent No. 0418175. Many literature methods are described for the preparation of orth-substituted benzoic acids. Where an ortho-substituent is introduced to the benzene ring via lithiation of the ortho-position of the ring, for example using the methods reviewed by Snieckus et al, Chem. Rev. (1990) Vol. 9 (6) pp 880–931, the reaction invariably involves protecting the carboxylic acid group. Gschwend and Rodriguez, Organic Reactions, Volume 26, Chapter 1 p 68 state that the direct ortho lithiation of arylcarboxylic acids is generally not feasible because of the increased electrophilicity of the carboxylate group. Where direct lithiation of aryl carboxylic acids is reported the reaction has been performed on non-phenyl ring systems, for example as described by S. Yu and B. Keay, J. Chem. Soc. (Perk. Trans. I) 1991, page 2600 to 2601 where 2-(t-butyldimethylsilyl)-3-furoic acid was lithiated in the four-position. In a number of literature references this problem is overcome by protecting the carboxylic acid group of the benzoic acid prior to lithiating the phenyl ring. For example Meyers et al, Tetrahedron Letters, (1983), Vol. 45 pp 4935–49 describe the use of an oxazoline protecting group to lithiate in the ortho position of a benzoic acid.

The present invention seeks to provide a method for introducing an ortho-substituent to a benzoic acid derivative via a lithiation in the ortho position without the need to protect the carboxylic acid group. This offers advantages by reducing the number of reaction steps needed to produce a required compound (since there is no need to introduce and subsequently remove a protecting group) for example by reducing the cost of synthesizing a compound (since there may be less synthetic steps in the reaction sequence) and by reducing the volume of waste chemicals that need to be disposed of in a reaction sequence.

SUMMARY OF THE INVENTION

Surprisingly the applicants have found that the direct ortho lithiation of certain benzoic acids may be achieved using a novel process. Thus, the invention provides a process for preparing ortho-substituted benzoic acids of formula (I):

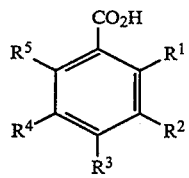

wherein:

$R^1$ is a group which may be introduced by electrophilic substitution of an aromatic lithio derivative;

$R^2$ is a fluorine, chlorine or bromine atom;

$R^3$ is a fluorine, chlorine bromine or hydrogen atom or a group selected from $R^6$, $-OR^6$ and $-SR^6$;

$R^4$ and $R^5$ are independently hydrogen, fluorine, chlorine, bromine, or a straight- or branched- chain alkyl group having from one to six carbon atoms optionally substituted by one or more fluorine atoms;

$R^6$ is a straight- or branched- chain alkyl group having from one to six carbon atoms optionally substituted by one or more halogen atoms;

with the proviso that when $R^4$ is fluorine, chlorine or bromine and $R^5$ is hydrogen, $R^2$ and $R^4$ represent the same group;

which comprises the reaction of a compound of formula (II)

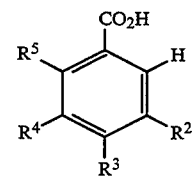

wherein $R^2$, $R^3$, $R^4$ and $R^5$ are as defined above, with a lithiating reagent, followed by the reaction of the ortho-lithiated compound thus obtained with an electrophilic reagent to introduce the group $R^1$.

It will be understood that the proviso in the above process is prevents the reaction leading to a mixture of ortho-substituted isomers which would subsequently require separation.

DETAILED DESCRIPTION OF THE INVENTION

As discussed above, the process of the invention removes the need to protect a benzoic acid prior to lithiating in the ortho position. The reaction is generally performed under an inert atmosphere at a temperature from −78° C. to 0° C., preferably from −78° C. to −20° C. A temperature range from −70° C. to −40° C. is also preferred. It will be understood that on a commercial scale a temperature range from −20° C. to 0° C. is generally preferred.

The reaction is generally performed in an inert solvent such as diethyl ether or more preferably tetrahydrofuran. The lithiation is typically carried out using alkyl lithium reagent such as n-butyllithium or sec-butyllithium, optionally in the presence of a catalyst or chelating agent, for example tetramethylethylene-diamine. Alternatively the lithiation may be carried out using a lithium amide base such as lithium di-isopropylamide, lithium hexamethyldisilazane or lithium tetramethylpiperidide. When one or more of the substituents $R^2$ to $R^5$ is bromine preferably a lithium amide base is used.

$R^1$ is a group which may be introduced by electrophilic substitution of an aromatic lithio derivative. Examples of such groups are;

alkyl groups such as a straight- or branched- chain alkyl group having from one to six carbon atoms excluding tertiary alkyl groups such as t-butyl;

alkenyl or alkynyl groups preferably alkenyl or alkynyl groups having from three to six carbon atoms;

alkylsulfenyl groups such as $-SR^6$;

arylsulfenyl groups such as -SAr, wherein Ar is phenyl group optionally substituted by from one to five groups selected from $R^6$, fluorine, chlorine, $-OR^6$ and $-SR^6$;

halogen atoms such as chlorine or bromine;

carboxylic acid or ester groups such as $-CO_2R^7$, wherein $R^7$ is a hydrogen atom or a group $R^6$;

aldehyde or ketone groups such as $-COR^8$, wherein $R^8$ is a hydrogen atom, $R^6$ or Ar;

carbinol groups such as $-C(OH)R^7R^8$;

trialkylsilyl groups such as $Si(R^6)_3$.

Preferably $R^1$ is a halogen atom, a straight- or branched- chain alkyl group having from one to six carbon atoms; or a group $-SR^6$;

More preferably $R^1$ is methyl, ethyl, bromine or $-SR^6$ wherein $R^6$ is methyl or ethyl.

Preferably $R^3$ is fluorine, chlorine, bromine, trifluoromethyl or methoxy.

In a further preferred embodiment $R^4$ and $R^5$ simultaneously represent hydrogen.

Generally the molar ratio of lithiating reagent: compound of formula (II) in the reaction to produce the ortho-lithiated compound is at least 2:1, preferably from 2.1 to 2.5:1, more preferably from 2.1 to 2.3:1.

Typically the reaction to produce the ortho-lithiated compound will take from 2 hours to 48 hours, preferably from 4 to 24 hours. It will be understood that the reaction time will vary according to the temperature of the reaction, the reactivity of the compound of formula (II) and the lithiating reagent used.

The electrophilic reagent used may be for example:

alkyl, alkenyl or alkynyl halides or dialkyl sulfates such as methyl iodide, allyl bromide or diethyl sulfate;

dialkyl or diaryl disulfides such as dimethyl disulfide or diphenyl disulfide;

halogens such as chlorine or bromine, N-halosuccinimides such as N-bromosuccinimide or other sources of electrophilic halogen such as hexachloroethane 1,1,2,2,-tetrachloro-1,2,-dibromoethane or 1,1,2,2-tetrabromoethane;

carbon dioxide or a chloroformate ester such as ethyl chloroformate;

a dialkyl or alkyl aryl formamide such as N,N-dimethyl formamide or N-methyl-N-phenyl formamide;

an acyl halide or anhydride such as acetyl chloride or acetic anhydride;

an aldehyde or ketone of formula $R^7C(O)R^8$ such as acetone or benzaldehyde, or a halotrialkyl silane such as chlorotrimethyl silane.

A number of the benzoic acids produced by this process are novel and as such constitute a further feature of the invention, in particular the following compounds:
3,4-dichloro-2-methylsulfenylbenzoic acid;
4-chloro-3-fluoro-2-methylbenzoic acid;
3-chloro-2-methylsulfenyl-4-trifluoromethylbenzoic acid;
4-chloro-3-fluoro-2-methylsulfenylbenzoic acid;
3-chloro-4-methoxy-2-methylsulfenylbenzoic acid;
3-chloro-4-fluoro-2-methylsulfenylbenzoic acid;
4-bromo-3-chloro-2-methylsulfenylbenzoic acid; and
4-bromo-3-fluoro-2-methylsulfenylbenzoic acid.

The following non-limiting Examples illustrate the invention.

EXAMPLE 1 n-Butyllithium (2.5M in hexane, 35 ml) was added with cooling to a solution of 3,4-difluorobenzoic acid (5.5 g) in dry tetrahydrofuran under an inert atmosphere maintaining the temperature below $-70°$ C. The mixture was stirred for 2 hours at $-70°$ C. A solution of dimethyl disulfide (19.8 g) in tetrahydrofuran was added and the mixture was stirred at $-70°$ C. for 1.5 hours. It was allowed to warm to room temperature, diluted with ether and washed with water. The aqueous layer was acidified to pH 1, extracted with ether, washed with water, dried (anhydrous $MgSO_4$) and filtered. The filtrate was evaporated to dryness and the residue was recrystallized from a mixture of cyclohexane and ether to give 3,4-difluoro-2-(methylsulfenyl)-benzoic acid (5.9 g) as a white solid, m.p. 149.2°–149.6° C.

By proceeding in a similar manner the following compounds of formula I were prepared:

| $R^1$ | $R^2$ | $R^3$ | $R^4$ | $R^5$ | Electrophilic Reagent | Reaction temp | m.p./°C. |
|---|---|---|---|---|---|---|---|
| MeS | Cl | Cl | H | H | (MeS)$_2$ | $-70°$ C. | 120–124 |
| Me | Cl | Cl | H | H | MeI | $-70°$ C. | 181–182 |
| Me | F | Cl | H | H | MeI | $-40°$ C. | 172–173 |
| MeS | Cl | CF$_3$ | H | H | (MeS)$_2$ | $-40°$ C. | 97–100 |
| MeS | F | Cl | H | H | (MeS)$_2$ | $-40°$ C. | 145–146 |
| MeS | Cl | OMe | H | H | (MeS)$_2$ | $-70°$ C. | 171 |
| MeS | Cl | F | H | H | (MeS)$_2$ | $-70°$ C. | 115 |
| Me | Cl | H | H | H | MeI | $-70°$ C. | — |

EXAMPLE 2 n-Butyllithium (2.5M in hexane, 63 ml) was added to a solution of diisopropylamine in dry tetrahydrofuran while maintaining the temperature at 0° C. Once addition was complete the cooling bath was removed and the mixture stirred for 30 minutes at room temperature. The resulting solution of lithium di-isopropylamide (LDA) was then added to a solution of 4-bromo-3-fluorobenzoic acid (14.6 g) in tetrahydrofuran while maintaining the temperature at $-50°$ C. The mixture was then stirred for 5 hours at $-30°$ C. A solution of dimethyl disulfide (21 g) in tetrahydrofuran was then added and the cooling bath was removed and the mixture allowed to stir at room temperature overnight. The mixture was diluted with ether and washed with water. The aqueous layer was acidified to pH 1 with 2M hydrochloric acid and extracted with ether, washed with water, dried ($MgSO_4$) and filtered. The filtrate was evaporated to dryness and the residue triturated with petroleum spirit (b.p. 60°–80° C.) to give 4-bromo-3-fluoro-2-(methylsulfenyl)benzoic acid (14 g) as a white solid, m.p. 152°–154° C.

By proceeding in a similar manner from the appropriately substituted starting material 4-bromo-3-chloro-2-(methylsulfenyl)benzoic acid was prepared, m.p. 126°–129° C.

EXAMPLE 3

A solution of 1.6N n-butyl lithium in hexane (294 ml) was added to 71 ml of tetramethyl ethylene diamine (TMEDA) in tetrahydrofuran at −70° C. under an inert atmosphere. 3-Fluorobenzoic acid (30 g) in tetrahydrofuran was added and the mixture was stirred for one hour. Hexachloroethane (111.5 g) was added and the reaction mixture was stirred for two hours at −70° C. The reaction mixture was allowed to warm to 10° C. and acidified (to pH 1) with 3M hydrochloric acid solution, extracted with diethyl ether, dried (anhydrous magnesium sulphate) and concentrated to give a solid that was recrystallised from heptane/ethyl acetate to give 2-chloro-3-fluorobenzoic acid (26 g).

By proceeding in a similar manner from the appropriately substituted starting materials the following compounds of formula (I) were prepared:

| $R^1$ | $R^2$ | $R^3$ | $R^4$ | $R^5$ | Electrophilic Reagent | Reaction temp |
|---|---|---|---|---|---|---|
| MeS | Cl | H | H | H | $(MeS)_2$ | −70° C. |
| Cl | F | F | H | H | $C_2Cl_6$ | −70° C. |
| Cl | Cl | F | H | H | $C_2Cl_6$ | −70° C. |
| Br | Cl | H | H | H | $(CCl_2Br)_2$ | −70° C. |

REFERENCE EXAMPLE 1

A solution of 4-bromo-3-fluorotoluene (35 g) and sodium hydroxide (7.7 g) in pyridine and water was mechanically stirred and heated to reflux. Potassium permanganate (123 g) was added to the mixture over 2 hours. The resulting suspension was heated at reflux for a further 3 hours. The mixture was filtered hot through hyflo. The hyflo was washed with boiling water, followed by ethyl acetate. The cooled aqueous layer was acidified to pH 1 with concentrated hydrochloric acid and extracted with ethyl acetate. The organic extract was washed with water, dried (MgSO4) and filtered. The filtrate was evaporated to dryness and the residue triturated with petroleum spirit (bp 60°–80° C.) to give 4-bromo-3-fluorobenzoic acid as a white solid (21.25 g), m.p. 213°–215° C.

We claims:

1. A process for preparing ortho-substituted benzoic acids of formula (I):

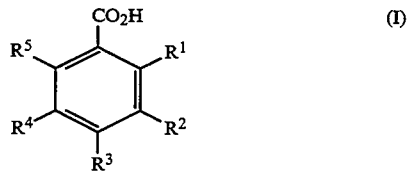

(I)

wherein:

$R^1$ is a group which may be introduced by electrophilic substitution of an aromatic lithio derivative;

$R^2$ is a fluorine, chlorine or bromine atom;

$R^3$ is a fluorine, chlorine, bromine or hydrogen atom or a group selected from $R^6$, $—OR^6$ and $—SR^6$, $R^4$ and $R^5$ are independently hydrogen, fluorine, chlorine, bromine, or a straight- or branched-chain alkyl group having from one to six carbon atoms optionally substituted by one or more fluorine atoms;

$R^6$ is a straight- or branched-chain alkyl group having from one to six carbon atoms optionally substituted by one or more halogen atoms;

with the proviso that when $R^4$ is fluorine, chlorine or bromine and $R^5$ is hydrogen, $R^2$ and $R^4$ represent the same group;

which comprises the reaction of a compound of formula (II):

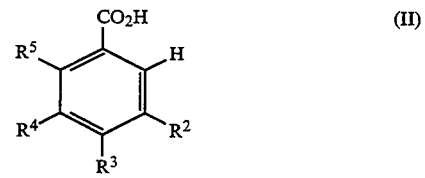

(II)

wherein $R^2$, $R^3$, $R^4$ and $R^5$ are as defined above, with a lithiating reagent, followed by the reaction of the ortho-lithiated compound thus obtained with an electrophilic reagent to introduce the group $R^1$.

2. The process according to claim 1 wherein the reaction is performed at a temperature from −78° C. to 0° C.

3. The process according to claim 1 wherein the reaction is performed at a temperature from −78° C. to −20° C.

4. The process according to claim 1 wherein $R^1$ is a halogen atom, a straight- or branched-chain alkyl group having from one to six carbon atoms; or a group $—SR^6$.

5. The process according to claim 4 wherein $R^1$ is methyl, ethyl, bromine or $—SR^6$ wherein $R^6$ is methyl or ethyl.

6. The process according to claim 1 wherein $R^3$ is fluorine, chlorine, bromine, trifluoromethyl or methoxy.

7. The process according to claim 1 wherein $R^4$ and $R^5$ simultaneously represent hydrogen.

8. The process according to claim 1 wherein the molar ratio of lithiating reagent: compound of formula (II) in the reaction to produce the ortholithiated compound is at least 2:1.

9. The process according to claim 8 wherein the molar ratio of lithiating reagent: compound of formula (II) is from 2.1 to 2.5:1.

10. The process according to claim 8 wherein the molar ratio of lithiating reagent: compound of formula (II) is from 2.1 to 2.3:1.

11. The process according to claim 1 wherein the lithiating reagent is an alkyl lithium reagent.

12. The process according to claim 1 wherein the lithiating reagent is a lithium amide base.

* * * * *